United States Patent [19]

Roos et al.

[11] 4,256,636

[45] Mar. 17, 1981

[54] AZO-DI-ISOBUTYRIC ACID-(N,N-HYDROXYALKYL)-AMIDINES

[75] Inventors: Ernst Roos; Herbert Bartl, both of Odenthal; Klaus Schuster, Leverkusen; Adolf Schmidt, Cologne, all of Fed. Rep. of Germany

[73] Assignee: Bayer Aktiengesellschaft, Fed. Rep. of Germany

[21] Appl. No.: 76,235

[22] Filed: Sep. 17, 1979

[30] Foreign Application Priority Data

Sep. 21, 1978 [DE] Fed. Rep. of Germany ....... 2841045
Sep. 21, 1978 [DE] Fed. Rep. of Germany ....... 2841046

[51] Int. Cl.³ .......................................... C07C 123/00
[52] U.S. Cl. .................................................. 260/192
[58] Field of Search ........................... 260/192, 564 R

[56] References Cited

U.S. PATENT DOCUMENTS 2,599,299  6/1952  Upson ................................. 260/192

FOREIGN PATENT DOCUMENTS 1198782  7/1970  United Kingdom .
1402060  8/1975  United Kingdom .

OTHER PUBLICATIONS

Houben–Weyl Methoden, der Organischen Chemie 1952(4th), Verlag; Stuttgart, p. 702–705.

*Primary Examiner*—Arthur P. Demers
*Attorney, Agent, or Firm*—Connolly and Hutz

[57] ABSTRACT

An azo di-isobutyric acid-(N,N'-hydroxyalkyl)-amidine corresponding to the formula (I):

$$\begin{array}{c} HO-R-N \\ HO-R' \end{array} C-C-N=N-C-C \begin{array}{c} N-R-OH \\ R'-OH \end{array} \quad (I)$$

with $CH_3$ groups on the central carbons and N–X groups at the ends.

in which
R and R', which may be the same or different, represent linear or branched alkylene radicals containing from 2 to 4 carbon atoms, and
X represents R'–OH or H.

They may be produced by reacting an azo-di-isobutyric acid iminoalkyl ether containing from 1 to 4 carbon atoms in the alkyl group with at least one monoalkanolamine containing from 2 to 4 carbon atoms or with a mixture of at least one monoalkanolamine and at least one dialkanolamine each containing from 2 to 4 carbon atoms in an alkanol radical, the molar ratio of monoalkanolamines to dialkanolamines in the mixture amounting to substantially 1:1, in substantially equivalent quantitative ratios at a temperature in the range of from 0° to 50° C. The amidines may be used as polymerization initiators, as cross-linking agents and as blowing agents in the production of foams.

7 Claims, No Drawings

AZO-DI-ISOBUTYRIC ACID-(N,N-HYDROXYALKYL)-AMIDINES

This invention relates to new azo-di-isobutyric acid-(N,N'-hydroxyalkyl)-amidines and to their use as polymerisation initiators, as crosslinking agents and as blowing agents in the production of foams.

U.S. Pat. No. 2,599,299 describes a process for producing the dihydrochloride of azo-di-isobutyric acid amidine.

In addition, German Auslegeschrift No. 1,693,164 describes a process for producing acid-free azo-di-isobutyric acid amidine. In this known process, however, special precautions have to be taken to ensure that the water-moist product does not decompose.

The use of these compounds as polymerisation initiators has also been described (cf. U.S. Pat. No. 2,599,300).

However, these compounds have never been adopted for use on a commercial scale both on account of the instability of the initiators themselves and on account of the corrosion and coagulation problems involved in their use as initiators. This is attributable above all to the hydrolysis of the free amidine group which leads to ammonia, amide groups and ammonium salt groups:

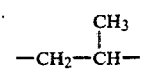

R=residue of the initiator molecule.

Whereas the solubility of the above-mentioned radical formers in water is basically a highly desirable property for polymerisation in aqueous suspensions or emulsions, the appearance of salts frequently interferes with the polymerisation reaction. In the case of sensitive emulsions, this can give rise to premature undesirable coagulation of the emulsions. Furthermore, the incorporation of salt-like groups in the polymer formed also causes problems in many cases and can have an extremely adverse effect upon the properties of the polymer.

It has now surprisingly been found that the disadvantages referred to above can be obviated by using new azo-di-isobutyric acid-(N,N'-hydroxyalkyl)-amidines corresponding to the formula (I):

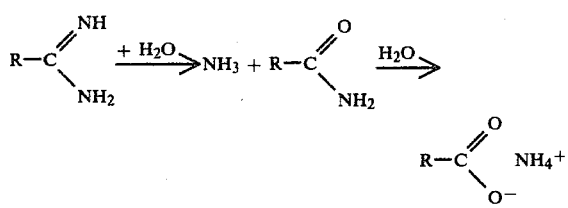 (I)

in which
R and R'—which may be the same or different—represent linear or branched alkylene radicals containing from 2 to 4 carbon atoms, and
X represents hydrogen or —R'—OH,
as polymerisation initiators. In addition, polymers having very special and desirable properties through incorporation of the hydrophilic hydroxyalkyl groups are obtained.

In the formula (I), R and R' preferably represent linear or branched alkylene radicals containing 2 or 3 carbon atoms such as —CH$_2$—CH$_2$—; —CH$_2$—CH$_2$—CH$_2$— or $$-CH_2-\underset{\underset{CH_3}{|}}{CH}-$$

and X preferably represents hydrogen or R'—OH.

R and R' in the formula (I) most preferably are the same and represent a linear alkylene radical containing 2 carbon atoms (=ethylene radical) whilst X most preferably represents hydrogen or a β-hydroxyethyl radical.

The present invention relates to the azo-di-isobutyric acid-(N,N'-hydroxyalkyl)-amidines corresponding to the formula (I) above and to their use as radical formers in the polymerisation of unsaturated compounds and/or in the crosslinking of polyunsaturated polymerisable compounds.

The azo-di-isobutyric acid-(N,N'-bis-hydroxyalkyl)-amidines and azo-di-isobutyric acid-(N,N'-tris-hydroxyalkyl)-amidines according to the invention may be produced by (A) reacting azo-di-isobutyric acid amidine unsubstituted on the N-atoms or the amidine substituted on the N-atoms by 1 to 5 hydroxyalkyl radicals containing from 2 to 4 carbon atoms, with alkylene oxides (C$_2$–C$_4$), or (B) reacting azo-di-isobutyric acid iminoalkyl ethers corresponding to the general formula (II) below with monoalkanolamines or with mixtures of monoalkanolamines and dialkanolamines.

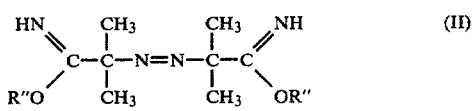 (II)

In the formula (II), R" represents lower alkyl radicals containing from 1 to 4 carbon atoms.

The reaction of azo-di-isobutyric acid iminomethyl ether with monoethanolamine [reaction scheme (IIIa)] and the reaction of azo-di-isobutyric acid iminoethyl ether with a mixture of mono- and di-ethanolamine [reaction scheme (IIIb)] are shown by way of example in the following:

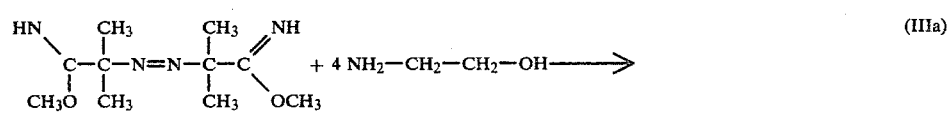 (IIIa)

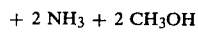
-continued

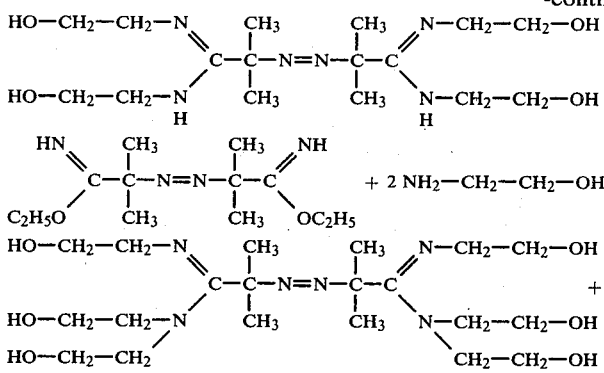

It is readily possible to produce azo-di-isobutyric acid-(N,N'-bis- or N,N'-tris-hydroxyalkyl)-amidines by initially subjecting azo-di-isobutyric acid amidine to a partial reaction with an alkylene oxide, followed by condensation with mono- and/or di-alkanolamine up to the required degree of substitution, or vice versa. On the other hand, the imino groups of the azo-di-isobutyric acid iminoalkyl ether may initially be completely or partly reacted with an alkylene oxide and the alkyl ether groups and residual imino groups, if any, subsequently condensed with mono- and/or di-alkanolamine to form the N,N'-bis-(hydroxyalkyl)- or N,N',N'-tris(hydroxyalkyl)-amidine of azo-di-isobutyric acid.

The azo-di-isobutyric acid-(N,N'-bis- or N,N',N'-tris-hydroxyalkyl)-amidines are preferably obtained by reacting azo-di-isobutyric acid iminoalkyl ether with mono-alkanolamines or with mixtures of monoalkanolamines and dialkanolamines (molar ratio 1:1).

The addition reaction with the alkylene oxides and the condensation reaction with mono- and/or di-alkanolamine is carried out at 0° to 50° C. and preferably at 20° to 45° C. The reactions may be carried out in the absence of solvents or in the presence of organic solvents which are inert to the reactants under the reaction conditions, for example in alcohols such as methanol or ethanol; in ethers such as diethyl ether or dioxane; in ketones such as acetone or ethylmethyl ketone; and also in aliphatic or aromatic hydrocarbons. The reactions may be carried out in the absence of applied pressure or under pressures of up to 50 bars.

Suitable alkylene oxides are ethylene oxide, propylene oxide, 1,2-epoxy butane, 2,3-epoxy butane and 1,2-epoxy-2-methyl propane, preferably ethylene oxide and propylene oxide and, more particularly, ethylene oxide.

The following amines may, e.g., be used for the reaction with the iminoalkyl ethers: ethanolamine, diethanolamine, 1-amino-2-propanol, bis-(2-hydroxypropyl)-amine, 1-amino-3-propanol, bis-(3-hydroxypropyl)-amine, isopropanolamine, diisopropanolamine, 1-amino-4-butanol, bis-(4-hydroxybutyl)-amine, 1-amino-3-butanol, bis-(3-hydroxybutyl)-amine, 1-amino-2-butanol, bis-(2-hydroxybutyl)-amine, 1-amino-2-methyl-2-propanol, bis-(2-hydroxy-2-methylpropyl)-amine, 2-amino-2-methyl-1-propanol, bis-(monohydroxy tert.-butyl)-amine, 1-amino-2-methyl-3-propanol and bis-(3-hydroxy-2-methylpropyl)-amine, or mixtures of the above-mentioned amines.

It is preferred to use ethanolamine, diethanolamine, 1-amino-2-propanol, bis-(2-hydroxypropyl)-amine, 1-amino-3-propanol, bis-(3-hydroxypropyl)-amine, isopropanolamine, diisopropanolamine or mixtures thereof; ethanolamine or diethanolamine or mixtures thereof are particularly preferred.

The alkylene oxides are preferably used in such quantities that approximately 1 mole of alkylene oxide is present per imino group of the amidines or iminoethers and approximately 2 moles of alkylene oxide per amino group of the amidines. The alkanolamines and dialkanolamines are preferably used in a quantity of 1 mole per imino, amino or alkylether group of the amidines or iminoethers.

The reaction of iminoalkyl ethers with amines to form amidines is known in principle from the literature (cf. Methoden der organischen Chemie, Houben-Weyl, 4th Edition (1952), Vol. 8, page 703); as is the hydroxyalkylation of amidines with alkylene oxides (cf. U.S. Pat. No. 2,980,554, column 3, lines 41 to 43).

The production of the azo-di-isobutyric acid iminoalkyl ethers used as starting materials is also known from the literature and may be carried out, for example, by the process according to German Offenlegungsschrift No. 2,242,520 (pages 31 to 32).

The following are mentioned as examples of the azo-di-isobutyric acid-(N,N'-hydroxyalkyl)-amidines produced by the cited processes:
azo-di-isobutyric acid-(N,N'-bis-2-hydroxyethyl)-amidine,
azo-di-isobutyric acid-(N,N'-bis-3-hydroxypropyl)-amidine,
azo-di-isobutyric acid-(N,N'-bis-2-hydroxypropyl)-amidine,
azo-di-isobutyric acid-(N-2-hydroxyethyl-N'-3-hydroxypropyl)-amidine,
azo-di-isobutyric acid-(N-2-hydroxyethyl-N'-2-hydroxypropyl)-amidine,
azo-di-isobutyric acid-(N,N'-bis-3-hydroxybutyl)-amidine,
azo-di-isobutyric acid-(N,N',N'-tris-2-hydroxyethyl)-amidine,
azo-di-isobutyric acid-(N,N',N'-tris-3-hydroxypropyl)-amidine,
azo-di-isobutyric acid-(N,N',N'-tris-2-hydroxypropyl)-amidine,
azo-di-isobutyric acid-(N-2-hydroxyethyl-N',N'-bis-3-hydroxypropyl)-amidine
azo-di-isobutyric acid-(N-2-hydroxyethyl-N',N'-bis-2-hydroxypropyl)-amidine,
azo-di-isobutyric acid-(N-3-hydroxypropyl-N',N'-bis-2-hydroxyethyl)-amidine, and
azo-di-isobutyric acid-(N-2-hydroxypropyl-N',N'-bis-2-hydroxyethyl)-amidine.

The azo-di-isobutyric acid-(N,N'-hydroxyalkyl)-amidines are obtained in a smooth high-yield reaction under the above-mentioned reaction conditions and are water-soluble, yellow to yellow-orange oils. They may be used as radical formers in the polymerisation of unsaturated compounds. They may also be used in the crosslinking of, or in crosslinking processes involving, unsaturated compounds or products, optionally with foaming. They are also suitable for use as blowing agents in the production of foams.

The use of the azo-di-isobutyric acid-(N,N'-hydroxyalkyl)-amidines in the production of aqueous polymer dispersions is described in the following and in Examples 7 to 19.

Polymer dispersions are frequently prepared for use as coating materials or, in combination with pigments and fillers, as coatings for wood, metals, ceramics, plastics materials and the like. If the coatings are to adhere firmly to the substrate, even in a moist atmosphere or in the presence of water, the content of water-soluble salts in a polymer film has to be as low as possible.

The salts not only impair the adhesion of the films to the substrate, but they also promote separation of the film from the surface. This is particularly critical when the polymer is hard and substantially non-tacky. In this case, small quantities of salts have a particularly serious affect upon the coalescence of the latex particles. In the presence of water, the salts passing into solution build up osmotic pressures at the diffusion interfaces of the latex particles which can give rise to chalking of the binder and can cause it to soften to the point where it dissolves.

Accordingly, it has been proposed to carry out polymerisation with hydrogen peroxide or with water-soluble, non-salt-like derivatives of perhydrol, such as tert.-butyl hydroperoxide. However, the latices obtained in this way show very poor ion and shear stability. In addition, it has frequently been recommended to carry out polymerisation with very small quantities of persulphates. Unfortunately, this leads to substantially non-reproducible latices, which, in some cases, can completely coagulate.

It has now been found that polymer dispersions can be obtained without the assistance of inorganic salts which adversely affect the adhesion and resistance to water of the polymers, providing azo-di-isobutyric acid-(N,N'-hydroxyalkyl)-amidines corresponding to the formula (I) above are used as polymerisation initiators instead of the usual alkali metal or ammonium persulphates or other salt-like peroxy compounds.

These amidines are a valuable addition to the already known water-soluble α,α'-azo-(α-methyl-γ-sulpho)-butyric acid dinitrile (IV) (cf. German Auslegesschrift No. 1,111,395), to the azodinitriles of the α,α'-azo-(α-methyl-γ-diethylamino)-butyric acid dinitrile type (V) (cf. U.S. Pat. No. 2,605,260) and of the γ,γ'-azo-(γ-cyano)-valeric acid=α,α'-azo-(α-methyl-γ-sulpho)-butyric acid dinitrile type (VI) (cf. U.S. Pat. No. 2,520,338) or, finally, to the 2,2'-azo-(2-methylpropionamidine), (VII), (cf. U.S. Pat. Nos. 2,599,299 and 2,599,300).

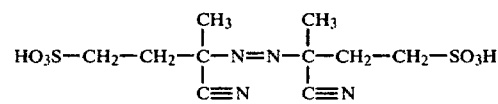

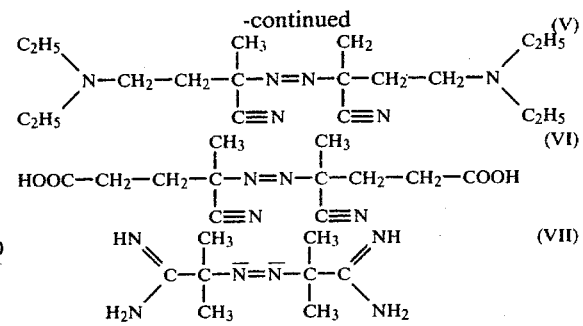

The amidines corresponding to the formula (VII) are generally used in the form of hydrochloric acid salts (cf. U.S. Pat. No. 2,599,300). However, they have to be used in ice-cooled form in order to avoid undesirable decomposition and hydrolysis (cf. the example of the production of a polyethylene latex with the amidine of an azodinitrile in: Houben-Weyl, Methoden der Organischen Chemie, 4th Edition, Vol. XIV/1 (1961), pages 222 et seq.). However, chloride ions are particularly troublesome in a latex intended for corrosion prevention, because they accelerate rust formation to a considerable extent. In addition, the amidines of the formula (VII) can only develop a favourable effect in a neutral or acid mixture.

By contrast, the initiators according to the invention corresponding to the formula (I) above are stable in aqueous solution at room temperature. They are active both in acid and in alkaline medium and are highly soluble in water.

The compounds of the formula (VI) are only soluble in an alkaline or neutral medium and are unsuitable for monomers which are to be polymerised in an acid or mildly acid medium.

The initiators according to the invention have a major advantage over the compounds corresponding to the formula (V), i.e. they contain in the molecule free OH-groups which are incorporated at the beginning and end of a polymer chain. These OH-groups provide for improved adhesion, are accessible as reactive groups for crosslinking reactions are are desirable for numerous applications.

Although the compounds corresponding to the formula (IV) give stable latices, the sulpho groups which they introdue into the polymer adversely affect the resistance to water of the films obtainable from dispersions such as these. In addition, the acid groups of the initiators corresponding to the formula (IV) have to be buffered with bases so that, ultimately, they do not have any particular advantages over the potassium or ammonium persulphate normally used.

The initiators according to the invention corresponding to the formula (I) may be used in alkaline medium and also in acid medium. Even when used in small quantities, they lead to high yields of polymer, as can be seen from the Examples.

It has proved to be particularly advantageous to use the initiators corresponding to the formula (I) in the form of salts or adducts of polymerisable acids. This measure enables polymerisation to be carried out at any pH-values in the range of from about 3 to 9. Examples of suitable polymerisable acids are monoolefinically unsaturated carboxylic acids containing from 3 to 5 carbon atoms, such as acrylic acid, methacrylic acid, crotonic acid, maleic acid and itaconic acid. It is also possible to use semiesters of maleic acid, itaconic acid and fumaric acid containing from 1 to 18 carbon atoms in the alcohol component. Vinyl sulphonic acid, methallyl sulphonic acid or 2-N-acrylamido-2-methyl propane sulphonic acid may also be used for adjusting the pH-value in cases where the electrolyte stability of the dispersions is of primary importance.

Finally, the alkaline reaction of the initiators corresponding to the formula (I) may also be reduced by additions of alkyl sulphonic acids and/or alkylaryl sulphonic acids, in which case salts with emulsifier properties are formed. Aliphatic monocarboxylic acids may also be used with advantage.

Polymerisation with the initiators corresponding to the formula (I) is preferably carried out at temperatures in the range of from 50° to 90° C. and, more particularly, at temperatures of from 50° to 80° C. and in the absence of applied pressure or under pressures of up to 200 bars.

The initiators may be used in quantities of from 0.2 to 10% by weight, based on the monomer total. In general, they are used in quantities of from 0.3 to 2% by weight. Where importance is attached to an increased incorporation of hydroxyl groups and to a low molecular weight, correspondingly higher quantities are used.

The initiators may be added in various ways during the polymerisation reaction. The initiator may be linearly added at a rate which just compensates for the decomposition of the initiators at the particular polymerisation temperature applied. However, the entire quantity of initiator may also be introduced at the outset. Alternatively, most of the initiator may be kept for the last fractions of monomer. The products obtained differ in their molecular weight distribution and in their properties according to the manner in which the initiator is added.

In the case of dispersions which are to be used as binders for the production of aqueous stoving lacquers, it is favourable, for example, to add most of the OH-group-containing initiators of the formula (I) towards the end of the introduction of the monomers so that polymer fractions of high molecular weight and low in hydroxyl groups are obtained at the beginning of polymerisation, whereas low molecular weight polymer fractions which improve levelling and gloss and which, by virtue of their higher terminal hydroxyl group content, can be effectively crosslinked with formaldehyde resins are obtained towards the end of polymerisation.

It has now surprisingly been found that the stability of the polymer dispersions produced with the initiators according to the invention is extremely good, even when anionic emulsifiers are used, although the incorporation of cationic groups into a polymer can generally be expected to give rise to flocculations where anionic emulsifiers are present.

Accordingly, standard anionic, non-ionic or cationic emulsifiers may be added in addition to the polymerisation initiators according to the invention. Standard cationic, anionic or non-ionic emulsifiers are described, for example, in Methoden der Organischen Chemie, Houben-Weyl, 4th Edition (1961), Vol. XIV/1, pages 190-208 and 4th Edition (1959), Vol. II/2, pages 113-138 and in "Surface Active Agents" by A. M. Schwartz and J. W. Perry, Interscience Publ. Inc., New York, 1958, pages 25 to 171. Combinations of anionic emulsifiers with non-ionic emulsifiers in a ratio of from 7:3 to 3:7 (molar ratio) or corresponding combinations of cationic emulsifiers with non-ionic emulsifiers are also possible.

However, polymerisation may also be carried out in the absence of standard emulsifiers in cases where compounds which form oligomers with an emulsifier-like effect or which perform a dual function of emulsifier and monomer are used.

Compounds such as these are, for example, alkali metal or ammonium or amine salts of maleic acid semiesters with an alcohol residue containing more than 5 carbon atoms, for example maleic acid cyclohexyl semiester/maleic acid dodecyl semiester salts. However, polymerisation may also be carried out in the absence of emulsifiers using protective colloids, such as polyvinyl alcohol for example.

Suitable polymerisable monomers are any olefinically unsaturated monomers which can be polymerised in the usual way with azodiisobutyronitrile in non-aqueous solution, for example styrene, α-methyl styrene, butadiene, acrylic acid esters containing from 1 to 8 carbon atoms in the alcohol component, methacrylic acid esters containing from 1 to 8 carbon atoms in the alcohol component, acrylonitrile, methacrylonitrile, vinyl chloride, vinylacetate, ethylene, chloroprene, etc.

In addition to the above-mentioned monomers, water-soluble compounds, such as methacrylic acid, acrylic acid, maleic acid semiester, itaconic acid and itaconic acid semiester, acrylamide, methacrylamide, etc., may also be incorporated in the polymers in smaller quantities. It is also possible to use comonomers still containing functional groups, for example OH-groups or epoxy groups, such as β-hydroxyethyl (meth)acrylate, β-hydroxypropyl (meth)acrylate, glycidyl (meth)acrylate and N-methylol- or N-methylol-alkyl ethers of (meth)acrylic acid amide.

The polymer dispersions may be used for a variety of applications. The way in which the new initiators act is illustrated in Examples 7 to 19, although the potential applications of the polymer dispersions are in no way limited by these Examples.

Where the described dispersions are film-forming, they are eminently suitable for coatings, particularly for coatings required to show increased anti-corrosion activity, improved behaviour in the salt-spray test, firm adhesion, improved compatibility and crosslinking with products containing methylol or methylol ether groups, for example with aminoplasts, such as melamine-formaldehyde resins or urea-formaldehyde resins, or phenoplasts, such as resols.

In the context of the invention, polymers are understood to be homopolymers and copolymers. Copolymers are understood to be not only copolymers with copolymerised monomers in statistical distribution or block copolymers, but also graft copolymers in which monomers have been grafted onto a preformed homopolymer or copolymer. Of the copolymers, statistical copolymers are preferred.

Azo-di-isobutyric acid-(N,N'-hydroxyalkyl)-amidines corresponding to the formula (I) are also eminently suitable for homogeneous-phase polymerisation processes known per se, i.e. preferably solution and bulk polymerisation processes. However, polymerisation may also merely begin in homogeneous phase, the polymer accumulating in finely divided form during the polymerisation reaction (precipitation polymerisation).

Virtually any olefinically unsaturated monomers which may be used for polymerisation with radical-forming azo compounds are suitable for homopolymerisation and copolymerisation in homogeneous phase. The following are examples of monomers such as these:

(a) α,β-monoolefins containing from 2 to 8 carbon atoms, such as ethylene, propylene, 1-butene, isobutylene and diisobutylene;

(b) conjugated diolefins containing from 4 to 6 carbon atoms, such as butadiene, isoprene, 2,3-dimethyl butadiene and 2-chlorobutadiene, preferably butadiene;

(c) (meth)acrylic acid, (meth)acrylonitrile, (meth)acrylamide, alkyl (meth)acrylates containing from 1 to 18 and preferably from 1 to 8 carbon atoms in the alcohol component, such as methyl acrylate, ethyl acrylate, propyl acrylate, isopropyl acrylate, n-butyl acrylate, tert.-butyl acrylate, 2-ethylhexyl acrylate, stearyl acrylate and the corresponding methacrylic acid alkyl esters, preferably acrylic acid, acrylonitrile, acrylamide, methylacrylate, butylacrylate, tert.-butylacrylate, 2-ethylhexylacrylate, methyl methacrylate;

(d) vinyl esters of organic monocarboxylic acids, the acid component containing from 1 to 18 and preferably from 2 to 4 carbon atoms, such as vinyl acetate and vinyl propionate, preferably vinyl acetate;

(e) monoolefinically unsaturated halogenated hydrocarbons, such as vinyl chloride or vinylidene chloride, preferably vinyl chloride;

(f) aromatic vinyl compounds, such as styrene, o-or p-methyl styrene, α-methyl styrene, α-methyl-p-isopropyl styrene, α-methyl-m-isopropyl styrene, p-chlorostyrene, preferably styrene. In this case, it is preferred always to use the less polymerisable monomers, such as α-methylstyrene and m- or p-isopropyl-α-methyl styrene, in admixture with at least one other of the copolymerisable monomers mentioned.

(g) Monoesters of α,β-monoolefinically unsaturated monocarboxylic acids containing 3 or 4 carbon atoms with dihydric saturated aliphatic alcohols containing from 2 to 4 carbon atoms, such as 2-hydroxyethyl methacrylate, 2-hydroxypropyl methacrylate, 4-hydroxybutyl methacrylate, 2-hydroxyethyl acrylate, 2-hydroxypropyl acrylate, 4-hydroxybutyl acrylate;

(h) N-methylol ethers of acrylic and methacrylic acid amide corresponding to the general formula (VIII):

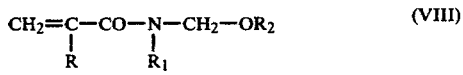

in which
R represents hydrogen or methyl,
$R_1$ represents hydrogen, alkyl, aralkyl or aryl,
$R_2$ represents alkyl or cycloalkyl, such as methyl, ethyl, n-propyl, isopropyl, n-butyl, isobutyl or cyclohexyl (cf. German Auslegeschrift No. 1,035,363).

It is preferred to use the N-methylol methylether of methacrylic acid amide. The monomers of group (h) are used and incorporated into the copolymer in quantities of from 1 to 20% by weight, based on the monomer total.

(i) Diesters and monoesters of α,β-monoolefinically unsaturated $C_3$-$C_5$-dicarboxylic acids, such as maleic acid, fumaric acid and itaconic acid, with 1 to 18 carbon atoms in the alcohol component, and also maleic acid anhydride, maleic or fumaric acid, amides of maleic and fumaric acid, maleic imides and unsaturated copolymerisable polyesters which contain the residues of maleic and/or fumaric acid as polymerisable constituents. Maleic acid anhydride is preferred.

(j) Vinylalkyl ethers containing from 1 to 4 carbon atoms in the alkyl group, such as vinylmethyl ether, vinylethyl ether, vinylpropyl ether, vinylbutyl ether.

(k) Crosslinking monomers containing several unconjugated olefinically unsaturated carbon-carbon bonds, such as divinyl benzene, diallyl phthalate, divinyl adipate, acrylic and/or methacrylic acid allyl ester, methylene-bis-acrylamide, methylene-bis-methacrylamide, triallyl cyanurate, triallyl isocyanurate, triacryloyl perhydro-S-triazine, bis-acrylates and bis-methacrylates of glycols and polyglycols containing from 2 to 20 carbon atoms, such as ethylene glycol di(meth)acrylate, propylene glycol di(meth)acrylate, butylene glycol-1,4-di(-meth)acrylate, tetraethylene glycol di(meth)acrylate, and tris-(meth)acrylates of trimethylol propane and glycerol.

The crosslinking monomers of group (k) are preferably used for copolymerisation in quantities of from 0.1 to 12% by weight, based on the monomer total. They are incorporated into the copolymer in the same quantities.

In addition, primary, secondary or tertiary aminoalkyl esters of (meth)acrylic acid preferably containing from 2 to 4 carbon atoms in the alkyl group and glycido(meth)acrylate may also be used as comonomers and may optionally be crosslinked through the amino or epoxide group during or after copolymerisation.

Monomers of groups (b), (c), (d), (e), (f), and (i) are preferably used for copolymerisation.

Where polymerisation is carried out in solution, water and organic solvents, for example dimethyl formamide, tert.-butanol, chlorobenzenes, etc., may be used as solvents.

The polymerisation reaction may be carried out at temperatures of from 50° C. to 90° C. and preferably at temperatures of from 55° C. to 75° C., depending on the decomposition characteristic of the azo compounds according to the invention. The quantity in which the initiator is used may be adapted to the required molecular weight and may amount to be between 0.05 and 10% by weight or more, based on the monomers used. It is, of course, also possible to deviate from these figures on the quantity of initiator and the temperature. The polymerisation reactions in homogeneous phase may be carried out in the absence of pressure or under pressures of up to 1500 bars.

In every case, the polymers obtained contain at least 2 hydroxyl groups, emanating from the initiator fragments, incorporated at the beginning and end of each polymer chain.

The introduction of hydroxyl groups at the beginning and end of polymer chains is of considerable practical importance to a variety of properties. On the one hand, the reactivity of the polymers enables them to be reacted with compounds which generally react with hydroxyl groups and form wide-mesh networks. Compounds such as these are, for example, polyisocyanates, polyepoxides, polycarboxylic acid anhydride, and compounds containing methylol and/or methylol ether groups. In addition, the hydroxyl groups considerably improve the adhesion of polymer films.

Examples 20 to 27 illustrate bulk and solution polymerisation reactions using the azo-di-isobutyric acid-(N,N'-hydroxyalkyl)-amidines corresponding to the formula (I).

The parts and percentages quoted in the Examples are by weight, unless otherwise indicated. The intrinsic viscosity [η], [dl/g] was measured in the solvents indicated at a temperature of 25° C.

Production of the azo-di-isobutyric acid-(N,N'-hydroxyalkyl)-amidines

EXAMPLE 1

Azo-di-isobutyric acid-(N,N'-bis-2-hydroxyethyl)-amidine 114 g (0.5 mole) of azo-di-isobutyric acid iminomethyl ether, 300 ml of methanol and 122 g (2 moles) of ethanolamine were stirred for 8 hours at 50° C. To remove methanol and ammonia (1 mole), the mixture was distilled out in a water jet vacuum (12 mbar) at temperatures of up to at most 50° C., leaving 165 g=88.2% of the theoretical yield of a yellow-orange, water-soluble oil; $n_D^{20}$ 1.4880.

Analysis calculated for $C_{16}H_{34}N_6O_4$, molecular weight 374: calculated C: 51.34%; H: 9.09%; N: 22.46%; O: 17.11%. observed C: 51.5%; H: 9.3%; N: 22.8%; O: 17.4%.

EXAMPLE 2

Azo-di-isobutyric acid-(N,N',N'-tris-2-hydroxyethyl)-amidine (two-stage process)

8.8 g (0.2 mole) of ethylene oxide were introduced while cooling with ice/water at 20° to 30° C. into 37.4 g (0.1 mole) of the azo-di-isobutyric acid-(N,N'-bishydroxyethyl)-amidine obtained in accordance with Example 1. The mixture was then stirred for 5 hours at room temperature (approximately 25° C.). A yellow, viscous, water-soluble oil ($n_D^{20}$ 1.4910) was obtained in a yield of 46 g, or 99% of the theoretical yield.

Analysis calculated for $C_{20}H_{42}N_6O_6$, molecular weight 462: Calculated C: 51.95%; H: 9.09%; N: 18.18%; O: 20.78%. observed C: 52.2%; H: 9.2%; N: 18.5%; O: 20.4%.

The same azo-di-isobutyric acid-(N,N',N'-tris-2-hydroxyethyl)-amidine is also obtained by the following process according to Example 3:

EXAMPLE 3

Azo-di-isobutyric acid-(N,N',N'-tris-2-hydroxyethyl)-amidine (one-stage process)

45.6 g (0.2 mole) of azo-di-isobutyric acid iminoethyl ether, 200 ml of methanol, 42 g (0.4 mole of diethanolamine and 26 g (0.4 mole) of ethanolamine were stirred for 8 hours at 50° C. To remove methanol and ammonia (0.4 mole), the mixture was distilled out in vacuo (12 mbar) at temperatures of up to at most 50° C., leaving 91 g=98% of the theoretical yield of a yellow, viscous, water-soluble oil which had the same refractive index as the oil of the preceding Example and was identical therewith.

EXAMPLE 4

Azo-di-isobutyric acid-(M,N'-bis-2-hydroxypropyl)amidine 57 g (0.25 mole) of azo-di-isobutyric acid iminomethyl ether, 200 ml of methanol and 75 g (1 mole) of 1-amino-2-propanol were heated for 8 hours to 50° C. in a water bath, 0.5 mole of ammonia being released. The mixture was distilled at 50° C., first under a pressure of 12 mbar and then under a pressure of 0.1 mbar in order to remove the volatile fractions. A yellowish water-soluble oil ($n_D^{20}$: 1.4691) was left behind as a residue in a quantity of 93 g, corresponding to a yield of 87% of the theoretical.

Analysis calculated for $C_{20}H_{42}N_6O_4$, molecular weight 430: calculated C: 55.81%; H: 9.76%; N: 19.53%; O: 14.88%. observed C: 56.1%; H: 10.0%; N: 19.7%; O: 14.7%.

If the 1-amino-2-propanol in the above mixture is replaced by 1-amino-3-propanol, azo-di-isobutyric acid(N,N'-bis-3-hydroxypropyl)-amidine is obtained in the form of a yellow oil which, on standing, solidifes into a yellowish paste.

EXAMPLE 5

Azo-di-isobutyric acid-(N,N'-bis-3-hydroxybutyl)-amidine 45.6 g (0.2 mole) of azo-di-isobutyric acid iminomethyl ether, 200 ml of methanol and 73.2 g (0.8 mole) of 1-amino-3-butanol were heated for 8 hours to 40° C., 0.4 mole of ammonia being released. The mixture was distilled at 50° C., first under a pressure of 12 mbar and then under a pressure of 0.1 mbar to remove the volatile fractions. A yellow oil ($n_D^{20}$:1.4801) was left behind as a residue in a quantity of 91 g corresponding to a yield of 93% of the theoretical.

Analysis calculated for $C_{25}H_{50}N_6O_4$, molecular weight 486: calculated C: 59.26%; H: 10.29%; N: 17.28%; O: 13.13%. observed C: 59.1%; H: 10.5%; N: 17.4%; O: 13.6%.

EXAMPLE 6

Azo-di-isobutyric acid-(N-2-hydroxypropyl-N',N'-bis-2-hydroxyethyl)-amidine 128 g (0.5 mole) of azo-di-isobutyric acid iminoethyl ester, 400 ml of methanol, 75 g (1 mole) of 1-amino-2-propanol and 105 g (1 mole) of bis-(2-hydroxyethyl)amine were heated for 8 hours to 50° C., 1 mole of ammonia being released. The mixture was distilled, first at 50° C./12 mbar and then at 50° C./0.1 mbar to remove the volatile constituents. A yellow water-soluble oil ($n_D^{20}$: 1.4780) was left behind as a residue in a quantity of 224 g, corresponding to 92% of the theoretical.

Analysis calculated for $C_{22}H_{46}N_6O_6$, molecular weight 490: calculated C: 53.88%; H: 9.39%; N: 17.14%; O: 19.59%. observed C: 53.6%; H: 9.7%; N: 17.0%; O:19.8%.

Application Examples 7 to 19 relating to the production of aqueous polymer dispersions

EXAMPLE 7

The emulsion polymerisation reaction is carried out in a 4-liter 5-necked flask of Jena glass equipped with a Dimroth reflux condenser, a gas-bubble counter (with a three-way cock between condenser and sealing fluid), a water-cooled stirrer (with a drive motor and centrifugally spreading blades at 90° intervals apart) provided with a nitrogen inlet cock and a group thermometer or thermosensor cartridge inserted into the flask.

Two Anschütz heads are fitted to the two remaining ground necks, either carrying four dropping funnels with pressure equalisation for the introduction of solutions I to IV specified hereinafter or having one dropping funnel for solution I and three feed spouts (consisting of a ground cap and core of a glass dropping tube which is centrally fused in, being bent downwards at its upper end and provided with a cock). The hoses leading via three miniature metering pumps to the supply vessels for solutions or mixtures II, III and IV are then optionally connected to these closeable feed spouts.

The solution of initial reaction mixture is then introduced into the flask. After the flask has been evacuated through the three-way cock (with the cocks of the feed spouts and the nitrogen feedpipe closed), nitrogen is introduced for equalisation. A T-tube with a non-return valve incorporated in the nitrogen feed pipe and dipping into water prevents excess pressure from building up in the glass flask.

Evacuation and gassing with nitrogen are carried out three times, after which all the air has been displaced from the reaction zone. The initial reaction mixture is then heated with stirring (approximately 250 to 300 rpm) to the required polymerisation temperature (70° C.) under a slight nitrogen excess pressure (two bubbles per second).

To this end, the flask is immersed in a thoroughly insulated waterbath with an overflow which can be heated by an immersion heater and cooled through a valve, which allows cold water to flow in, the maximum heating rate and maximum cooling rate substantially corresponding to one another.

The immersion heater and cooler are manipulated variables of a control system of which the controlled variable is the internal temperature (i.e. the temperature of the dispersion) and of which the disturbance variable is primarily the exothermic reaction.

In this way, the internal temperature can be very accurately adjusted. The deviation from the required temperature is less than 1°, given a uniform reaction.

Once the required polymerisation temperature has been reached, solution I is added all at once, after which polymerisation generally begins immediately. When a blueish seed latex has formed and when the heat of polymerisation has abated, solutions II, III, IV are added dropwise over a certain period, in this case 6 hours, or are pumped in through suitable miniature metering pumps which is more accurate.

After all the components have been added, the polymerisation mixture is after-polymerised for a certain time (in this case 2 hours) at a certain temperature (in this case 85° C.) in order to complete conversion of the monomers.

|  | g | parts by weight, based on total components |
|---|---|---|
| Initial reaction mixture: | | |
| Fully desalted or distilled water | 930.0 | 33.646 |
| Sodium lauryl sulphate | 6.0 | 0.217 |
| Acrylic acid-n-butyl ester | 64.2 | 2.323 |
| Acrylonitrile | 17.05 | 0.617 |
| Styrene | 17.05 | 0.617 |
| Methacrylamide | 4.0 | 0.144 |
| Solution I | | |
| Distilled water (or fully desalted water) | 81.0 | 2.930 |
| Azo-di-isobutyric acid-(N,N'-bis-2-hydroxyethyl)-amidine | 2.5 | 0.090 |
| Methacrylic acid, 50% in water | 2.2 | 0.077 |
| Solution II | | |
| Acrylic acid-n-butyl ester | 715.2 | 25.875 |
| Acrylonitrile | 189.9 | 6.87 |
| Styrene | 189.9 | 6.87 |
| Methacrylamide | 45.7 | 1.6533 |
| Solution III | | |
| Water (see above) | 270.0 | 9.768 |
| Azo-di-isobutyric acid-(N,N'-bis-2-hydroxyethyl)-amidine | 7.0 | 0.253 |
| Methacrylic acid, 50% in water | 6.2 | 0.224 |
| Solution IV | | |
| Water (see above) | 195.0 | 7.091 |
| Sodium lauryl sulphate | 20.2 | 0.731 |
| Sum total | 2,764.1 | 100 |

Polymerisation temperature: 70°C.
Addition time for Solutions II, III, IV: 6 hours
After-polymerisation: 2 hours at 85° C.

The thinly liquid latex obtained in this way has a solids content of from 45 to 46% and passes freely through a 30$\mu$ square-mesh Perlon cloth, only a little coarse-grained coagulate (approximately 0.5 to 5 g) being retained.

The latex has uniform particles approximately 130 nm in diameter. It dries at 25° C. to form a clear, non-tacky, highly water-resistant film.

A drop of water left on the surface of the film for about 30 minutes does not cloud or dissolve the film. In order to improve its ion resistance, the latex may be aftertreated with non-ionic emulsifiers. However, this is only necessary for special applications.

The latex may be mixed with standard commercially available water-soluble melamine-formaldehyde resins or urea-formaldehyde resins of the type used for stoving lacquers. In addition, pigments and fillers may be added to these mixtures. Through the absence of the inorganic solvents normally used, aqueous stoving systems of the type in question show improved resistance to water and adhesion to various substrates, particularly metals.

The polymer on which the latex is based is gel-free, soluble in tetrahydrofuran or dimethyl formamide and has an intrinsic viscosity [$\eta$] of 3.0 dl/g at 25° C. in tetrahydrofuran.

It consists of:

62.7% of polymerised butyl acrylate units
16.65% of acrylonitrile units
16.65% of styrene units
4.0% of methacrylamide units.

EXAMPLE 8 (Comparison)

(A) The procedure is as in Example 7, except that the initiator is replaced by the same quantity of ammonium peroxy disulphate. The coagulate-free latex formed is yellow in colour. Clear films of this latex show poorer adhesion to glass and are more sensitive to water. In analogous combination with pigments, melamine-formaldehyde resin mixtures prepared with this latex give distinctly poorer results on storage in water. The layers stoved onto metal separate from the substrate.

(B) The procedure is as in Example 7, except that the initiator is replaced by the same quantity of $\gamma,\gamma'$-azo-($\gamma$-cyano)-valeric acid (formula VI) dissolved in an equivalent quantity of dilute aqueous 10% ammonia solution. The latex has a particle size of approximately 150 nm, is distinctly yellow in colour and contains approximately 15 g of coagulate. The clear film dried at 25° C., to whose surface a drop of water was applied with a pipette, clouds and dissolves after about 30 minutes.

EXAMPLE 9

The procedure is as in Example 7, except that the initiator is replaced by azo-di-isobutyric acid-(N,N',N'-tris-2-hydroxyethyl)-amidine. A substantially monodisperse latex having similar properties to the latex described in Example 7 is obtained.

EXAMPLE 10

The solution described below as initial reaction mixture is introduced into the apparatus described in Example 7 and heated under nitrogen to 75° C. After Solution I has been injected, Solutions II, III and IV are introduced over a period of 5 hours, after which the temperature is increased to 80° C., followed by stirring for 2 hours.

A thinly liquid, coagulate-free latex having a solids content of 46.5% is obtained. After the residual monomers have been removed, the latex may be mixed with commercially available water-soluble urea-formaldehyde resins or melamine-formaldehyde resins and pigments and used as an aqueous stoving lacquer.

|  | g | parts by weight, based on total components |
|---|---|---|
| Initial reaction mixture: |  |  |
| Distilled water | 919.0 | 31.8971 |
| Sodium lauryl sulphate | 6.0 | 0.208 |
| Acrylic acid-n-butyl ester | 60.0 | 2.082 |
| Acrylonitrile | 15.0 | 0.5205 |
| Styrene | 15.0 | 0.5205 |
| Methacrylic acid-2-hydroxy propyl ester | 10.0 | 0.347 |
| Methylacrylamide | 2.0 | 0.0694 |
| Methacrylic acid | 2.0 | 0.0694 |
| Solution I |  |  |
| Distilled water | 100.0 | 3.471 |
| Azo-di-isobutyric acid-(N,N'-bis-2-hydroxyethyl)-amidine | 3.0 | 0.104 |
| Methacrylic acid, 50% in water | 2.64 | 0.0916 |
| Solution II |  |  |
| Acrylic acid-n-butyl ester | 700.0 | 24.296 |
| Acrylonitrile | 175.0 | 6.074 |
| Styrene | 175.0 | 6.074 |
| Methacrylic acid-2-hydroxy-propyl ester | 116.7 | 4.050 |
| Methacrylamide | 23.3 | 0.809 |
| Methacrylic acid | 23.3 | 0.809 |
| Solution II |  |  |
| Distilled water | 300.0 | 10.412 |
| Azo-di-isobutyric acid-(N,N'-bis-2-hydroxyethyl)-amidine | 7.0 | 0.243 |
| Methacrylic acid, 50% in water | 6.2 | 0.215 |
| Solution IV |  |  |
| Distilled water | 200.0 | 6.941 |
| Sodium lauryl sulphate | 20.0 | 0.694 |
| Sum total | 2,881.14 | 100 |

Polymerisation temperature: 75° C.
Addition time for Solutions II, III, IV: 5 h
After-polymerisation: 2 hours at 80° C.

Since the monomers are copolymerised substantially quantitatively, as in the following Examples, the integral composition of the polymer corresponds to the composition of the monomer mixture:

| 57.7% | by weight of butyl acrylate units |
|---|---|
| 14.45% | by weight of acrylonitrile units |
| 14.45% | by weight of styrene units |
| 9.6% | by weight of methacrylic acid-2-hydroxypropyl ester units |
| 1.9% | by weight of methacrylic acid units |
| 1.9% | by weight of methacrylamide units |
| 100% | by weight. |

EXAMPLE 11

400 Parts by weight of distilled water, 1 part by weight of an alkyl monosulphonate containing from 12 to 14 carbon atoms and 0.25 part by weight of azo-diisobutyric acid-(N,N'-bis-2-hydroxyethyl)-amidine are introduced into a three-necked flask and heated to 80° C.

50 Parts by weight of a mixture of 200 parts by weight of styrene, 275 parts by weight of acrylic acid-n-butyl ester and 25 parts by weight of methacrylic acid are then added. After stirring for 30 minutes at 80° C., the rest of the monomer mixture and a solution of 350 parts by weight of distilled water, 10 parts by weight of an alkyl monosulphonate containing from 12 to 14 carbon atoms and 5 parts by weight of azo-diisobutyric acid-(N,N'-bis-hydroxyethyl)-amidine are uniformly added dropwise over a period of 3 hours at a temperature of 80° C. followed by stirring for 2 hours at 80° C. 1230 Parts by weight of a coagulate-free dispersion are obtained after degassing. The dispersion has a solids content of 39% and a mean particle size of 145 nm. The flowout time from a DIN cup (2 mm orifice) amounts to 69 seconds.

EXAMPLE 12

The procedure is as in Example 11, except that the monomer mixture used in that Example is replaced by a mixture of 190 parts by weight of styrene, 260 parts by weight of acrylic acid-n-butyl ester, 25 parts by weight of methacrylic acid and 25 parts by weight of 2-hydroxypropyl methacrylate. Otherwise the conditions are the same. 1150 Parts by weight of a coagulate-free dispersion are obtained after degassing. The dispersion has a solids content of 39.5% and a mean particle size of 138 nm. The flowout time from a DIN cup (2 mm orifice) amounts to 78 seconds.

The dispersion thus obtained dries at 25° C. to form clear water-resistant films. It may be mixed with melamine-formaldehyde resins or urea-formaldehyde resins and pigments. The resulting mixtures may be stoved onto metals, forming firmly adhering, water-resistant and solvent-resistant coatings.

EXAMPLE 13

The procedure is the same as in Example 12 except that an equivalent quantity of azo-di-isobutyric acid-(N,N'-bis-2-hydroxypropyl)-amidine is used as initiator. 1190 parts by weight of a coagulate-free dispersion are obtained after degassing. The dispersion has a solids content of 37.5%, a mean particle size of 132 nm and a flow-out time from a DIN cup (2 mm orifice) of 75 seconds.

EXAMPLE 14

Polyvinyl chloride latex

3000 Parts by weight of distilled water, 7.5 parts by weight of an alkyl monosulphonate containing from 12 to 14 carbon atoms, 6 parts by weight of azo-di-isobutyric acid-(N,N',N'-tris-2-hydroxyethyl)-amidine and 10 parts by weight of acetic acid are introduced into a stainless-steel autoclave equipped with an anchor stirrer. The autoclave is evacuated, purged twice with nitrogen (3 bars) and then evacuated again. 1500 Parts by weight of vinyl chloride are then introduced into the autoclave and the internal temperature is increased to 65° C. This temperature is maintained for 12 hours. The initial pressure amounts to 13 bars. On completion of polymerisation, the pressure amounts to 4 bars.

4175 Parts by weight of a coagulate-free latex having a particle size of 180 nm are obtained after degassing. The polymer has an intrinsic viscosity of 0.77 (as measured in tetrahydrofuran). The solids content amounts to 29% and the flowout time from a DIN cup (2 mm orifice) to 75 seconds.

EXAMPLE 15

Polyvinyl acetate latex

A solution of 12.8 parts by weight of polyvinyl alcohol (partially hydrolysed polyvinyl acetate with a degree of hydrolysis of 88%) in 125 parts by weight of distilled water is prepared in a three-necked flask.

1. A solution of 0.35 part by weight of azo-di-isobutyric acid-(N,N'-bis-2-hydroxyethyl)-amidine in 40 parts by weight of distilled water and 0.8 part by weight of acetic acid, and 2. 191 Parts by weight of vinyl acetate, are simultaneously added dropwise to the solution heated to 68° C. over a period of 3.5 hours, during which the temperature is kept constant at 68° C. After stirring for another 3.5 hours at 68° C., a solution of 0.05 part by weight of azo-di-isobutyric acid-(N,N'-bis-2-hydroxyethyl)-amidine in 10 parts by weight of distilled water is added dropwise over a period of 15 minutes, followed by stirring for 45 minutes at 90° C.

350 Parts by weight of a highly viscous dispersion having a solids content of 51% and a mean particle size of 260 nm are obtained after degassing.

EXAMPLE 16

The procedure is as in Example 15 except that an equivalent quantity of azo-di-isobutyric acid-(N,N',N'-tris-2-hydroxyethyl)-amidine is used as initiator.

342 Parts by weight of a highly viscous dispersion having a solids content of 48% and a particle size of 245 nm are obtained.

EXAMPLE 17

Polychloroprene latex

120 Parts by weight of distilled water, 5 parts by weight of the sodium salt of a disproportionated abietic acid and 0.6 part by weight of sodium hydroxide are initially introduced into a three-necked flask. After purging with nitrogen for 30 minutes at room temperature, 100 parts by weight of a chloroprene stabilised with 180 ppm of phenothiazine are stirred in. The contents of the flask are then heated under nitrogen to 64° C., followed by the dropwise addition over a period of 2 hours of a solution of 2.5 parts by weight of azo-di-isobutyric acid-(N,N'-bis-2-hydroxyethyl)-amidine in 100 parts by weight of distilled water. The mixture is then stirred for 3 hours at 64° C. The unreacted chloroprene is removed by distillation with steam.

310 Parts by weight of a stable dispersion having a solids content of 25.5% and a mean particle size of 185 nm are obtained.

EXAMPLE 18

The procedure is as in Example 17 except that an equivalent quantity of azo-di-isobutyric acid-(N,N',N'-tris-2-hydroxyethyl)-amidine is used as initiator.

Removal of the unreacted chloroprene by distillation with steam leaves 290 parts by weight of a coagulate-free dispersion having a solids content of 27% and a mean particle size of 170 nm.

EXAMPLE 19

Styrene-butadiene latex

2700 Parts by weight of distilled water, 70 parts by weight of the sodium salt of a disproportionated abietic acid, 7.5 parts by weight of n-dodecyl mercaptan and 6 parts by weight of azo-di-isobutyric acid-(N,N'-bis-2-hydroxyethyl)-amidine are initially introduced into a stainless-steel autoclave equipped with an anchor stirrer. The autoclave is evacuated, purged twice with nitrogen (3 bars) and then evacuated again. 435 Parts by weight of styrene and 1065 parts by weight of butadiene are then successively pumped in. With the stirrer rotating at 150 rpm, the contents of the autoclave are heated to 65° C., the pressure amounting to 10.5 bars, and kept at this temperature for 10 hours. The pressure then amounts to 8.0 bars. On completion of the reaction, a solution of 1 part by weight of hydroquinone in 50 parts by weight of distilled water is introduced under pressure for stabilisation.

3450 Parts by weight of a coagulate-free latex are obtained after degassing. The latex has a solids content of 33%, a mean particle size of 190 nm and a flow-out time from a DIN cup (2 mm orifice) of 130 seconds.

Bulk and Solution Polymerisation (Examples 20 to 26)

EXAMPLE 20

In a glass bomb tube, a solution of 0.6 part by weight of azo-di-isobutyric acid-(N,N',N'-tris-2-hydroxyethyl)-amidine in 30 parts by weight of styrene is gassed with nitrogen for 3 minutes to remove the air present. After the bomb tube has been sealed by fusing, its contents are heated for 8 hours to 75° C.

The polymerised contents are dissolved in 300 parts by weight of tetrahydrofuran and subsequently precipitated with 10 times the quantity by weight of methanol. 17 parts by weight of purified polymer are obtained after drying in vacuo at 50° C.

Intrinsic viscosity (as measured in tetrahydrofuran): 0.49.

The polymers may be crosslinked with diisocyanates and polyisocyanates through the terminal hydroxyl groups incorporated.

2 Parts by weight of the polystyrene containing terminal hydroxyl groups obtained in accordance with Example 20 are dissolved in 18 parts by weight of anhydrous chlorobenzene. The solution is crosslinked with 0.2 part by weight of hexamethylene diisocyanate in the presence of 0.05 part by weight of tin (II) octoate.

After standing for 24 hours at room temperature, a crosslinked gel has formed. A film cast onto glass immediately after mixing is also crosslinked after drying for 24 hours.

EXAMPLE 21

A solution of 0.6 part by weight of azo-di-isobutyric acid-(N,N',N'-tris-2-hydroxyethyl)-amidine in 30 parts by weight of methyl methacrylate is polymerised in the same way as described in Example 20. After dissolution and reprecipitation, 19 g of polymer having an intrinsic viscosity in tetrahydrofuran of 0.45 are obtained.

EXAMPLE 22

A solution of 30 parts by weight of acrylonitrile, 70 parts by weight of dimethyl formamide and 0.3 part by weight of azo-di-isobutyric acid-(N,N'-bis-2-hydroxyethyl)-amidine is stirred for 6 hours at 80° C. in a three-necked flask equipped with a thermometer, reflux condenser and nitrogen feedpipe. The highly viscous solution formed is precipitated in 1000 parts by weight of water and dried in vacuo at 50° C.

15 Parts of a polymer having an intrinsic viscosity (as measured in dimethyl formamide) of 0.58 are obtained.

EXAMPLE 23

Following the procedure of Example 22, a solution of 30 parts by weight of vinyl acetate, 70 parts by weight of tert.-butanol, 0.3 part by weight of azo-di-isobutyric acid-(N,N'-bis-2-hydroxyethyl)-amidine and 2 parts by weight of acetic acid is stirred for 6 hours at 80° C. After the highly viscous solution has been precipitated in 1000 parts by weight of water, 13 parts by weight of a polymer having an intrinsic viscosity (as measured in dimethyl formamide) of 0.35 are obtained after drying.

EXAMPLE 24

500 Parts by weight of distilled water are introduced into a three-necked flask. The contents of the flask are then heated under nitrogen to an internal temperature of 70° C., after which (a) 100 parts by weight of acrylonitrile, and
(b) a solution of 0.5 part by weight of azo-di-isobutyric acid-(N,N'-bis-2-hydroxyethyl)-amidine in 50 parts by weight of distilled water, are uniformly added dropwise over a period of 2 hours. On completion of the dropwise addition, the mixture is stirred for 2 hours at 70° C. The polyacrylonitrile precipitated is filtered off under suction, washed thoroughly with water and dried at 50° C.

75 Parts by weight of polymer are obtained.

EXAMPLE 25

0.6 Part by weight of azo-di-isobutyric acid-(N,N'-bis-2-hydroxypropyl)-amidine is used as an initiator under the same test conditions as in Example 24.

62 Parts by weight of polymer are obtained.

EXAMPLE 26

Following the procedure of Example 20, a mixture of 22.5 parts of styrene and 7.5 parts of acrylonitrile is polymerised in the presence of 0.15 part of azo-di-isobutyric acid-(N,N'-bis-2-hydroxyethyl)amidine. Instead of tetrahydrofuran, dimethyl formamide is used as solvent for the copolymer. Drying in vacuo leaves 19 parts of purified copolymer consisting of 72% of styrene units and 28% of acrylonitrile units and having an intrinsic viscosity of 0.86, as measured in dimethyl formamide.

EXAMPLE 27

A mixture of 45 parts of styrene and 55 parts of n-butyl acrylate, 400 parts of chlorobenzene and 2 parts of azo-di-isobutyric acid-(N,N'-bis-3-hydroxybutyl)-amidine are polymerised in the same way as in Example 22, but for 6 hours at 75° C. The copolymer formed is precipitated from its chlorobenzene solution with 1500 parts of methanol and dried in vacuo at 50° C. 65 parts of a copolymer having 49% of styrene units and 51% of n-butylacrylate units and an intrinsic viscosity of 0.72, as measured in dimethyl formamide, are obtained.

Crosslinking of the copolymer through the OH-groups incorporated

2 Parts of the copolymer dissolved in 8 parts of anhydrous chlorobenzene are mixed with 0.05 part of tin(II) octoate and 0.2 part of isophorone diisocyanate. Films cast onto glass from this solution are crosslinked after 24 hours at room temperature and can no longer be dissolved by chlorobenzene.

We claim:

1. An azo-di-isobutyric acid-(N,N'-hydroxyalkyl)-amidine corresponding to the formula (I):

$$\begin{array}{c} HO-R-N \\ HO-R' \end{array} \diagdown C-\underset{\underset{CH_3}{|}}{\overset{\overset{CH_3}{|}}{C}}-N=N-\underset{\underset{CH_3}{|}}{\overset{\overset{CH_3}{|}}{C}}-C \diagup \begin{array}{c} N-R-OH \\ R'-OH \end{array} \quad (I)$$

in which
R and R', which may be the same or different, represent linear or branched alkylene radicals containing from 2 to 4 carbon atoms, and
X represents R'—OH or H.

2. A process for producing an azo-di-isobutyric acid-(N,N'-hydroxyalkyl)-amidine corresponding to the formula (I) as defined in claim 1, which comprises reacting an azo-di-isobutyric acid aminoalkyl ether containing from 1 to 4 carbon atoms in the alkyl group with at least one mono-alkanolamine containing from 2 to 4 carbon atoms or with a mixture of at least one monoalkanolamine and at least one dialkanolamine each containing from 2 to 4 carbon atoms in an alkanol radical, the molar ratio of monoalkanolamines to dialkanolamines in the mixture amounting to substantially 1:1, in substantially equivalent quantitative ratios at a temperature in the range of from 0° to 50° C.

3. A process for producing an azo-di-isobutyric acid-(N,N'-hydroxyalkyl)-amidine corresponding to the formula (I) as defined in claim 1, which comprises reacting an azo-di-isobutyric acid amidine, or an azo-di-isobutyric acid amidine of which the hydrogen atoms attached to the nitrogen atoms of the two amidine radicals are partly substituted by hydroxyalkyl radicals containing from 2 to 4 carbon atoms, with an alkylene oxide containing from 2 to 4 carbon atoms.

4. A modification of the process claimed in claim 2, wherein the imino groups of the azo-di-isobutyric acid iminoalkyl ether are initially completely or partly reacted with an alkylene oxide, and the alkyl ether groups and residual imino groups, if any, are subsequently condensed with a mono- and/or di-alkanolamine.

5. A modification of the process claimed in claim 3, wherein the azo-di-isobutyric acid amidine is initially subjected to a partial reaction with an alkylene oxide, followed by condensation with a mono- and/or di-alkanolamine up to the required degree of substitution, or vice versa.

6. A process for producing a compound of the formula (I), in which X represents R'—OH, which comprises reacting a compound of the formula (I), in which X represents H, with an alkylene oxide containing from 2 to 4 carbon atoms.

7. A process as claimed in claim 2, wherein, after the condensation of the azo-di-isobutyric acid iminoalkyl ether (1 mole) with a monoalkanolamine (4 moles) to form the azo-di-isobutyric acid-(N,N'-bis-hydroxyalkyl)-amidine, the azo-di-isobutyric acid-(N,N'-bis-hydroxyalkyl)-amidine thus obtained is reacted with 2 moles of an alkylene oxide containing from 2 to 4 carbon atoms to form an azo-di-isobutyric acid-(N,N',N'-tris-hydroxyalkyl)-amidine.

* * * * *